United States Patent [19]
Brandau

[11] Patent Number: 5,433,315
[45] Date of Patent: Jul. 18, 1995

[54] SUTURE MATERIAL PACK

[75] Inventor: Rolf Brandau, Homberg, Germany

[73] Assignee: B. Braun Melsungen AG, Melsungen, Germany

[21] Appl. No.: 338,283

[22] Filed: Nov. 14, 1994

Related U.S. Application Data

[63] Continuation of Ser. No. 162,451, Dec. 2, 1993, abandoned.

[30] Foreign Application Priority Data

Dec. 4, 1992 [DE] Germany ................ 42 40 831.8

[51] Int. Cl.⁶ ............................................. A61B 17/04
[52] U.S. Cl. ............................... 206/63.3; 206/382
[58] Field of Search ................ 206/63.3, 380, 382, 206/383, 339

[56] References Cited

U.S. PATENT DOCUMENTS

| 3,939,969 | 2/1976 | Miller et al. | |
| 4,089,409 | 5/1978 | Cerwin. | |
| 4,284,194 | 8/1981 | Flatau. | |
| 4,496,045 | 1/1985 | Ferguson et al. | 206/63.3 |
| 4,533,041 | 8/1985 | Aday et al. | 206/63.3 |
| 5,121,836 | 6/1992 | Brown et al. | 206/63.3 |
| 5,174,087 | 12/1992 | Bruno | 206/63.3 X |
| 5,271,494 | 12/1993 | Odesmatt et al. | 206/63.3 |

FOREIGN PATENT DOCUMENTS 0458432 11/1991 .

*Primary Examiner*—Jacob K. Ackun
*Attorney, Agent, or Firm*—Spensley Horn Jubas & Lubitz

[57] ABSTRACT

A suture material package includes a base panel for carrying the wound-up suture material which is clamped between a winding panel and a fold-over panel. The base panel is joined by a folding panel which in turn is joined by a thread holding panel. The folding panel and the thread holding panel are connected to each other by an oblique folding line. The end of the thread is fixed under a fixing flap of the thread holding panel. When the envelope containing the folding card is opened, the end of the thread slides out of the fixing flap and is exposed for being pulled out.

9 Claims, 2 Drawing Sheets

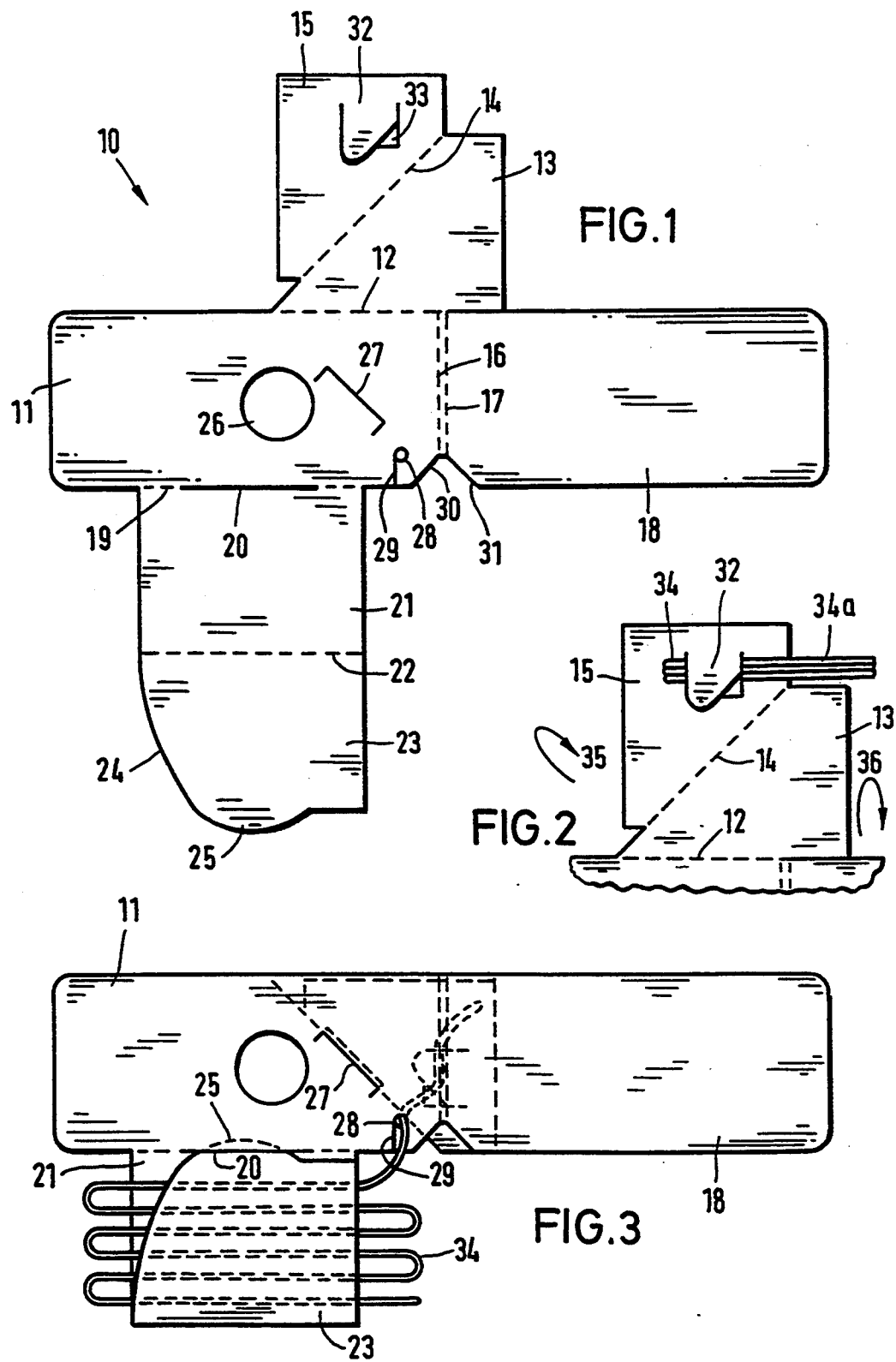

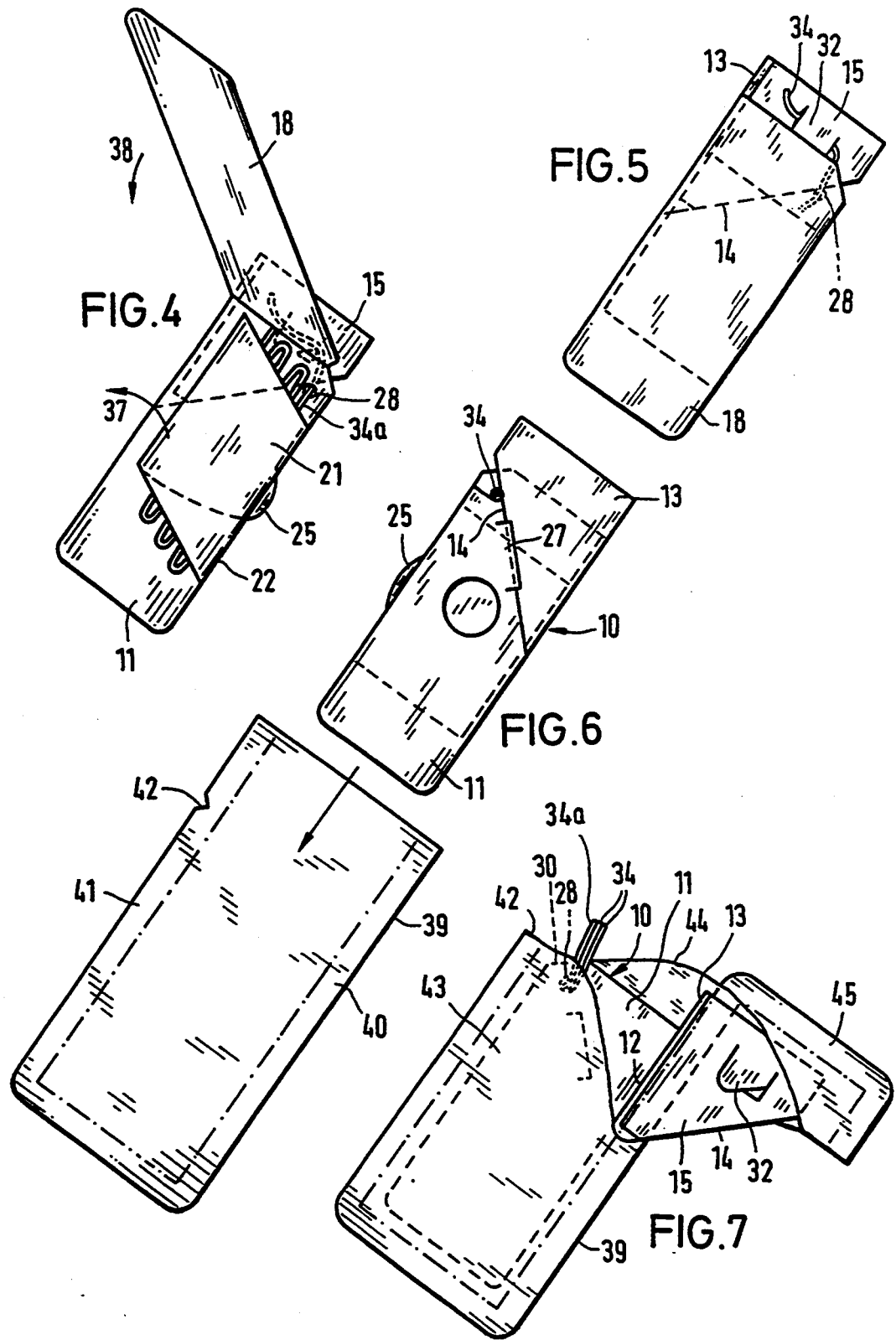

SUTURE MATERIAL PACK

This is a continuation of application Ser. No. 08/162,451 filed on Dec. 2, 1993, now abandoned.

BACKGROUND OF THE INVENTION

The invention is directed to a suture material package for surgical suture material wherein the suture material is contained in a folding card in such a manner that suture material can be pulled out therefrom in an easy and controlled fashion.

In a known suture material package disclosed in U.S. Pat. No. 3,939,969, the folding card comprises three elongate folding panels arranged laterally adjacent each other and being separated from each other by longitudinal folding lines. These folding panels are folded on top of each other and in their folded condition are inserted into a flat envelope which is closed by welding along its edges. For the withdrawal of thread material, the envelope is torn open starting at a longitudinal edge of the envelope, whereby also a part of the uppermost panel of the folding card is torn off and a length of the thread material is exposed, with the end of the thread being retained on a flap of an underlying panel. For withdrawing a length of thread, the end of the thread or the needle attached thereto has to be pulled out of the fixing flap. This is a bothersome procedure, particularly when the withdrawal of thread is performed with a hand clad in a surgical glove.

European Patent Application 0 458 432 A1 discloses a suture material package wherein the folding card comprises four panels arranged adjacent each other in a row, i.e. a needle holding panel, a cover panel, a winding panel and a fold-over panel to be folded into a position above the winding panel. The end of the thread connected to the needle is inserted into fixing flaps of the needle holding panel and projects in arcuate shape beyond the needle holding panel. Also in this known suture material package, it is required that, after opening an envelope surrounding the folded folding card, the end of the thread or the needle is manually gripped and freed from the fixing flaps before the thread can be pulled out of the folding card.

The co-pending U.S. patent application Ser. No. 07/897,276 describes a suture material package wherein a folding card has a base panel, a winding panel, a fold-over panel and a thread holding panel for holding the end of a thread. The thread holding panel has the same size as the base panel and, upon opening of the package, a part of the cover plate is torn off so that a part of the thread holding panel holding a portion of the thread is exposed. However, the end of the exposed thread is still captured under a flap of the thread holding panel and must be freed before the thread can be drawn off from the folding card.

It is an object of the invention to provide a suture material package wherein, on the one hand, the end of the thread is reliably held in place when the thread is inserted during the winding process and the thread coil is fixed in position after the winding process, and, on the other hand, withdrawal of thread by gripping the end of the thread is facilitated.

SUMMARY OF THE INVENTION

In the suture material package according to the invention, the thread holding panel with its fixing flap extends beyond the base panel, and when the envelope is torn open, the thread holding panel is pivoted around a longitudinal edge of the base panel whereby the end of the thread folded between the winding panel and the fold-over panel slides out of the fixing flap. Since the end of the thread is clamped on the pivotable thread holding panel in a manner allowing the thread to be pulled out, the end of the thread will become detached during the pivoting movement of the thread holding panel and then freely protrude from the still folded part of the folding card. Thus, the end of the thread is presented to the user while freely projecting from the folding card, i.e. without the need to first pull it out from a fixing means.

A considerable advantage resides in that, when winding the thread, the end of the thread is retained by the thread holding panel, with the take-up of the thread on the winding panel being performed by machine. Subsequently, the fold-over panel is folded over the winding panel for holding the thread supply in position. Then, the winding panel is folded onto one side and the thread holding panel is folded onto the other side of the base panel, the thread holding panel projecting beyond the end of the base panel. Therefore, the thread supply and the end of the thread are fixed during the folding process. In the folded condition, the folding card is introduced into the envelope, and the envelope is sealed by welding. When the envelope is torn open, the thread holding panel is pivoted to the side relative to the rest of the folding card whereby the end of the thread is released from the fixing flap and freely protrudes for being gripped.

Preferably, the thread holding panel is folded under a folding panel abutting the longitudinal edge of the base panel facing away from the winding panel. This folding panel is folded into a position under the base panel so that the fixing flap is located on the side of the thread holding panel facing towards the base panel, but projects beyond the base panel. The base panel can have a slitted hole formed therein for allowing the passage of the thread through the base panel. It is a further considerable advantage that the path of the thread in the folded condition of the folding card is unkinked so that no noteworthy friction will occur on the edges when the thread is pulled out.

When arranged in the folding card, the thread coil is kept fixed in position and is protected from mechanical damage. Preferably, the folding panel and the thread holding panel have their folding line extending obliquely (at an angle of 45°) to the base panel. In the folded condition of the folding card, this folding line acts as a bending line for controlling the tear-open process of the envelope. When the envelope is being torn open, the folding card is not destroyed and not even damaged.

An embodiment of the invention will be described in greater detail hereunder with reference to the drawings.

BRIEF DESCRIPTION OF THE DRAWINGS

FIG. 1 is a plan view of the folding card when folded into its spread-out configuration, FIG. 2 is a view of a detail from FIG. 1, the arrows showing the folding directions of the thread holding panel and the folding panel, FIG. 3 is a plan view of the folding panel after the winding process, FIG. 4 is a perspective view illustrating the further folding of the folding panel, FIG. 5 is a plan view of the completely folded folding panel, FIG. 6 is a plan view illustrating the insertion of the folding panel into the envelope, and FIG. 7 is a plan view illustrating the manner in which the envelope is torn open for withdrawal of thread.

DESCRIPTION OF THE PREFERRED EMBODIMENT

The folding card 10 shown in FIG. 1 consists of an integral blank of firm paper or cardboard material. Folding card 10 comprises a rectangular elongate base panel 11, with one of its longitudinal edges 12 forming a folding line joining a folding panel 13. The folding panel 13 is arranged along one half of base panel 11 and extends beyond base panel 11 in the longitudinal direction. Folding panel 13 is delimited by a folding line 14 oriented obliquely at an angle of 45° to the longitudinal direction of base panel 11. Folding line 14 has its prolongation abutting onto the longitudinal edge 12 of base panel 11 and is joined by the thread holding panel 15. The thread holding panel 15 is congruent with the folding panel 13 so that it can be folded into a position under the folding panel. Both panels 13 and 15 are substantially triangular.

The end of base panel 11 adjacent folding panel 13 is joined, through two parallel folding lines 16,17, by a cover panel 18 which is substantially of the same size as base panel 11 and can be folded into a position above base panel 11.

On the longitudinal edge of base panel 11 opposite longitudinal edge 12, there is arranged a folding line 19 with an insertion slit 20. Folding line 19 is joined to the winding panel 21 which has its opposite edge limited by a folding line 22 which in turn is joined by the fold-over panel 23. The winding panel 21 and the fold-over panel 23 are shorter than base panel 11, with both ends of base panel 11 extending beyond these two panels 21 and 23. Fold-over panel 23 is substantially congruent with winding panel 21; however, fold-over panel 23 has one of its edges provided with a rounded portion 24 and has its outer longitudinal edge provided with a flap 25 adapted for insertion into insertion slit 20.

Base panel 11 is formed with a centering hole 26 into which the center pin of a winding machine can be inserted for centering the folding card 10 in the winding machine. Further, base panel 11 is provided with a U-shaped punched locking flap 27 which is arranged obliquely at an angle of 45° to the longitudinal direction of the base panel and is adapted for having the folding edge formed by the folding line 14 inserted thereunder.

In the vicinity of one edge of base panel 11, there is formed a passage opening 28 which via a slot 29 merges into the longitudinal edge. The passage opening 28 is located at a corner opposite folding panel 13. This corner of base panel 11 has a beveled portion 30 and the adjacent corner of cover panel 18 has a beveled portion 31. Because of these beveled portions 30 and 31, the envelope can be reliably torn open in a controlled manner even if the folded folding card is not exactly in its correct position.

The thread holding panel 15 is provided with a punched-out fixing flap 32 for clamping the end of the thread. This fixing flap 32 is directed towards base panel 11. One of the edges of fixing flap 32 is delimited by an opening 33 which allows the thread end to easily slide out of fixing flap 32 when the envelope is being torn open.

With the folding card 10 being arranged in the condition shown in FIG. 1, the end of a thread 34 is fixed to folding card 10 by placing it under the fixing flap 32 as illustrated in FIG. 2 for thus clamping it tight. In FIG. 2, a plurality of thread ends are shown because the suture material in this Figure consists of a plurality of individual threads arranged in parallel to each other. The thread holding panel 15 is folded in the direction of arrow 35 around the folding line 14 and into a position under the folding panel 13 so that the fixing flap 32 along with the threads 34 will take a position on the backside. Then, the folding panel 13 is folded around the folding line 12 in the direction of arrow 36 into a position under base panel 11, and the edge formed by folding line 14 is shifted into a position under locking flap 27 of base panel 11. Thus, the fixing flap 32 together with the thread ends is located on the backside. The thread 34 is inserted through slit 29 into the passage opening 28 and laid onto the winding panel 21 in serpentine configuration. This process takes place in a winding machine which comprises pins (not shown) arranged on both ends of winding panel 21. The thread 34 is placed around these pins so as to follow the course shown in FIG. 3. After the thread has been laid in the above manner, the fold-over panel 23 is folded into a position above winding panel 21, and flap 25 is inserted into insertion slit 20 for securing the thread 34.

FIG. 4 illustrates the manner in which the winding panel 21 and the fold-over panel 23, lying on top of each other, are folded—around the folding line 22—onto base panel 11, with the thread holding panel 15 (together with folding panel 13) extending beyond one end of base panel 11. Without being kinked, the thread runs from the fixing flap 32, which is oriented in forward direction, through the passage opening 28 and inside the pocket formed by the winding panel 21 and the fold-over panel 23. The thread loops project out of said pocket on both ends thereof. The folding movement of the thread pocket onto base panel 11 is illustrated by arrow 37. Thereafter, cover panel 18 is laid onto the pocket formed by winding panel 21 and fold-over panel 23 (arrow 38).

FIG. 5 is a front view of the folding card in its folded condition, i.e. the folding card is seen from the same side as in FIGS. 1 to 3. The folding card is of rectangular, elongate shape and is slightly longer than the base panel 11 or the cover panel 18 because the thread holding panel 15 with the folding panel 13 extends beyond the base panel 11 and the cover panel 18 on one end. On this protruding end, the fixing flap 32 is provided for holding the end of the thread clamped thereunder. From this point, the thread runs through the passage opening 28.

FIG. 6 is a rear view of the folded folding card 10, the shown rear side of the folding card 10 being formed by the base panel 11 and the folding panel 13 folded into its position under base panel 11. The folding edge formed by the oblique folding line 14 has been shifted under the locking flap 27 of base panel 11.

As shown in FIG. 6, the folding card 10 is inserted into the envelope 39 which consists of a flat sheath of coated foil, having sealing seams 40 and 41 provided along its edges. After insertion of folding card 10 into the opening of the sheath, also this opening is closed by a sealing seam so that the folding card with the suture material is completely enclosed. A tear-off notch 42 is provided on one of the longitudinal edges of the envelope 39 for tearing open the envelope 39 at the height of the beveled portions 30,31 of folding card 10. When the envelope 39 is being torn open as shown in FIG. 7, the front foil 43 of envelope 39 will be ripped along the folding edge formed by the oblique folding line 14 while the rear foil is ripped open at random. In this manner, there is generated a pocket-shaped tear-off portion 45 of foil 39. This pocket contains the part of the folding panel 13 and of thread holding panel 15 extending beyond base panel 11 and cover panel 18. The folding panel 13 is pivoted into the open position around the longitudinal edge 12. At the same time, the end of thread 34 slides out of the fixing flap 32 to present itself to the user in the position shown in FIG. 7. For pulling the thread out of the folding card, it merely has to be gripped by the user's hand. When opening the envelope 39, the envelope will be destroyed, but the folding card 10 will be left undamaged.

I claim:

1. A suture material package, comprising:
   an envelope,
   a folded card enclosable within the envelope, the folded card comprising:
   a first panel defining a first longitudinal edge, a second longitudinal edge, a first side, and a second side,
   a second panel joined to the first panel along at least a portion of the second longitudinal edge,
   a third panel that is joined to the second panel and that is folded over onto the second panel to thereby retain suture material between the second panel and the third panel, and
   a fourth panel connected to the first panel along a common bendable edge and having a fixing flap for holding an end of a thread of suture material, the fourth panel extending beyond the first, second and third panels and being pivotable about the first longitudinal edge of the first panel, the second panel and the third panel being folded onto the first side of the first panel and the fourth panel being folded onto the second side of the first panel,
   whereby tearing open the envelope containing the folded card causes the fourth panel to pivot about the first longitudinal edge of the first panel and causes the end of the thread held in the fixing flap to slide out of the fixing flap while the suture material is retained between the second panel and the third panel.

2. The suture material package of claim 1, comprising:
   a fifth panel joined to the first longitudinal edge of the first panel, the fourth panel being folded onto the fifth panel.

3. The suture material package of claim 2, wherein the fourth panel is joined to the fifth panel along a folding line that extends substantially obliquely to the first longitudinal edge of the first panel.

4. The suture material package of claim 2, wherein the fifth panel is folded onto the second side of the first panel.

5. The suture material package of claim 3, wherein the folded card has an exterior and wherein the folding line along which the fifth panel and the fourth panel are joined is positionable on the exterior of the folded card and wherein the folding line provides a guide line along which the envelope is tearable.

6. The suture material package of claim 3, comprising:
   an oblique locking flap provided on the first panel for clamping the fifth panel and the fourth panel along the folding line.

7. The suture material package of claim 1, wherein a portion of the first panel near the second panel defines a slitted passage opening for the thread.

8. The suture material package of claim 1, comprising:
   a sixth panel, the sixth panel having an end that is joined to an end of the first panel and being configured to be folded over the second panel and the third panel, wherein the fifth panel extends beyond the first panel toward the sixth panel in a direction substantially parallel to the sixth panel.

9. The suture material package of claim 2, wherein the fourth panel and the fifth panel define a common folding line and wherein the fourth panel and the fifth panel are substantially congruent with respect to the common folding line.

* * * * *